United States Patent [19]
Lekholm

[11] Patent Number: 5,218,961
[45] Date of Patent: Jun. 15, 1993

[54] APPARATUS FOR IN VIVO INTRACARDIAL OF A MEASURED SIGNAL CORRESPONDING TO THE PHYSICAL ACTIVITY OF A SUBJECT AND A HEART PACEMAKER HAVING A STIMULATION RATE CONTROLLED THEREBY

[75] Inventor: Anders Lekholm, Bromma, Sweden

[73] Assignee: Siemens Aktiengesellschaft, Munich, Fed. Rep. of Germany

[21] Appl. No.: 761,288

[22] Filed: Sep. 17, 1991

[30] Foreign Application Priority Data

Sep. 28, 1990 [EP] European Pat. Off. ........ 90118714.6

[51] Int. Cl.⁵ ............................................. A61N 1/365
[52] U.S. Cl. ................ 128/419 PG; 128/634
[58] Field of Search ......... 128/634, 670, 736, 419 PG

[56] References Cited

U.S. PATENT DOCUMENTS

| | | | |
|---|---|---|---|
| 4,217,910 | 8/1980 | Khalil | 128/670 |
| 4,399,820 | 8/1983 | Wirtzfeld et al. | 128/419 PG |
| 4,408,613 | 10/1983 | Relyea | 128/670 |
| 4,554,927 | 11/1985 | Fussell | 128/670 |
| 4,763,655 | 8/1988 | Wirtzfeld et al. | 128/419 PG |
| 4,788,982 | 12/1988 | Gedeon et al. | 128/670 |
| 4,807,632 | 2/1989 | Liess et al. | 128/419 PG |

Primary Examiner—William E. Kamm
Attorney, Agent, or Firm—Hill, Steadman & Simpson

[57] ABSTRACT

An apparatus for the in vivo intracardial acquisition of a measured signal corresponding to the physical activity of a subject has an optoelectronic arrangement measuring the blood oxygen content of the subject and a temperature sensor for measuring the blood temperature. The apparatus can be operated so that a measured signal can be obtained which is optionally dependent on the blood oxygen content and the blood temperature, dependent only on the blood oxygen content, or dependent only on the blood temperature.

20 Claims, 2 Drawing Sheets

APPARATUS FOR IN VIVO INTRACARDIAL OF A MEASURED SIGNAL CORRESPONDING TO THE PHYSICAL ACTIVITY OF A SUBJECT AND A HEART PACEMAKER HAVING A STIMULATION RATE CONTROLLED THEREBY

BACKGROUND OF THE INVENTION

1. Field of the Invention

The present invention is directed to an apparatus for the intracardial acquisition of a measured signal corresponding to the physical activity of a subject, and in particular to an implantable apparatus for in vivo acquisition of such a signal.

2. Description of the Prior Art

Measuring instruments are required, for example, in cardiac pacemaker technology, for acquiring a measured signal corresponding to the physical activity of the subject in whom the pacemaker is implanted, for the purpose of adapting the rate with which the heart of the subject is stimulated to the physical activity of the subject. An apparatus of this type is described, for example, in European Application 0 249 822. This known measuring instrument includes means for forming a signal component corresponding to the blood oxygen content of the pacemaker user, by means of a light transmitter for emitting light into the blood of the user, and a light receiver for receiving the light reflected at the blood. The instrument also includes a temperature sensor for forming a signal component corresponding to the blood temperature. The instrument also includes a power supply circuit. Because the blood oxygen content proceeds to a saturation condition at a certain intensity of physical activity, the signal component corresponding to the blood oxygen content can only describe the physical activity of the subject with sufficient precision when the physical activity is at a relatively low intensity. By contrast, the body or blood temperature in the presence of physical activity represents a substantially exact indicator for the intensity of the physical activity. In the aforementioned known measuring instrument, the signal component corresponding to the blood oxygen content and the signal component corresponding to the blood temperature are combined (overlaid) in such a manner that a measured signal is obtained which can be reliably evaluated even with a high intensity of physical activity.

For the reason, the aforementioned known measuring instrument has an advantage over other known measuring instruments which supply either a signal corresponding only to the blood oxygen content or a signal corresponding only to the blood temperature. These other known measuring instruments responding only to the blood oxygen content or only to the blood temperature, however, also have advantages. It is possible to integrate the light transmitter, the light receiver and a temperature sensor in a catheter to be introduced into the heart of a subject, or to integrate those components into the electrode of a heart pacemaker. This does not present space problems because the light transmitter and the light receiver and the temperature sensor are extremely small components, however, the catheter must contain a line having at least four poles, or an electrode having at least four conductors must be used. It is also possible to integrate the drive circuit into the catheter or into the electrode, and for this purpose it is only necessary that the catheter contain a two-pole line or that the electrode have two conductors, however, integration of the drive circuit into the catheter or into an electrode in combination with the other components presents space problems.

SUMMARY OF THE INVENTION

It is an object of the present invention to provide an apparatus for in vivo intracardial acquisition of a measured value representing the physical activity of a subject which is optimally and versatilely adaptable to individual requirements.

It is a further object of the invention to provide such an apparatus which can reliably provide signals which are accurately representative of a wide range of physical activity intensities.

It is another object of the present invention to provide such an apparatus wherein the number of electrical connections which are necessary between a light transmitter, a light receiver and a temperature receiver, and a drive circuit, are as low as possible.

The above object is achieved in accordance with the principles of the present invention in an apparatus for in vivo intracardial acquisition of a measured signal corresponding to the physical activity of a subject having means for forming a signal component corresponding to the blood oxygen content in the form of a light transmitter for emitting light onto the blood of the subject and a light receiver for receiving light reflected from the blood, and a temperature sensor for the formation of a signal component corresponding to the blood temperature, and a drive circuit which provides a constant test current or a constant test voltage. The light transmitter, the light receiver and the temperature sensor are combined to form a two-terminal network through which the test current flows, or across which the test voltage drops, and the measured signal is derived from the voltage drop across the drive circuit or from the current drawn by the drive circuit. Dependent on the current or on the voltage at the output of the drive circuit, the intensity of the light from the light transmitter will change. Additionally, because the light receiver and the temperature sensor are electrically connected, the output of the light receiver will be temperature-dependent as well. Thus, the measuring instrument can be made more or less dependent on the blood oxygen content as well as more less dependent on temperature by suitable selection of the test current or the test voltage generated by the drive circuit. Appropriate selection of the test current or the test voltage will influence the signal components corresponding to the blood oxygen content, or will influence the signal component corresponding to the blood temperature so that one or the other can be made to predominate in the total signal, or a signal having both components identically present can be obtained.

As a consequence of the light transmitter, the light receiver and the temperature sensor being interconnected to form a two-terminal network, two connecting lines between this two-terminal network and the drive circuit are sufficient. This is advantageous because a two-pole line can be easily integrated into a catheter, and the alternative of the use of an electrode having two conductors is equally unproblematical. In the measuring instrument of the invention, therefore, there is no necessity to integrate the drive circuit into a catheter or into an electrode, and the space problems associated therewith are thus avoided.

In order to adapt the characteristics of the measuring instrument to changing requirements during its operation, a further embodiment of the invention includes means for adjusting the test current or the test voltage. In a preferred embodiment of the invention, the means for forming the signal component corresponding to the blood oxygen content includes a circuit component having a temperature coefficient which changes in a direction opposite to the response of the temperature sensor, and the test current or the test voltage can be set to a value such that the measured signal is independent of the blood temperature. Another preferred embodiment of the invention provides that the test current or the test voltage can be set to a value at which the optical operation of the means for forming the signal component corresponding to the blood oxygen content is reduced to such an extent that the measured signal becomes independent of the blood oxygen content. There is thus also the advantageous possibility of operating the measurement instrument in such a way that its characteristics correspond to a measuring instrument which is exclusively dependent on blood oxygen content or exclusively dependent on blood temperature.

The light transmitter and/or the light receiver may be photosemiconductors, and the temperature sensor may be a components whose resistance is temperature-dependent. Such components can be easily miniaturized, and therefore can be integrated easily into a catheter to be introduced into the heart of the subject, or in an intracardial electrode. Moreover, these types of component have a long useful life and the electrical characteristics thereof remain substantially constant over their useful life.

In the above-discussed preferred embodiment, a light emitting is provided as a light transmitter and a PTC resistor connected in series with the light emitting diode is provided as the temperature sensor. A phototransistor is provided as the light receiver, and is connected in parallel with the PTC resistor. A drive circuit is provided which delivers a constant test current. Because the forward conducting voltage of the light-emitting diode is substantially independent of current, but does have a temperature-dependency with a negative temperature coefficient, a value of the test current can be easily found at which the oppositely directed temperature responses of the light-emitting diode and of the PTC resistor cancel each other, and the measuring instrument thus supplies a measured signal which is independent of temperature. Moreover, the test current can be easily reduced to such a low value that the light-emitting diode emits no light, or emits light having such a low intensity, that the measured signal is independent of the blood oxygen content.

In a further embodiment of the invention the drive circuit generates a test current or a test voltage in pulsed form. This ensures that no heating of the measuring instrument will occur as a result of current flowing therethrough, which could falsify the measured signal.

The measuring instrument disclosed herein is preferably employed in a heart pacemaker whose stimulation rate is controlled dependent on the measured signal.

DESCRIPTION OF THE PREFERRED EMBODIMENTS

Figure 1:
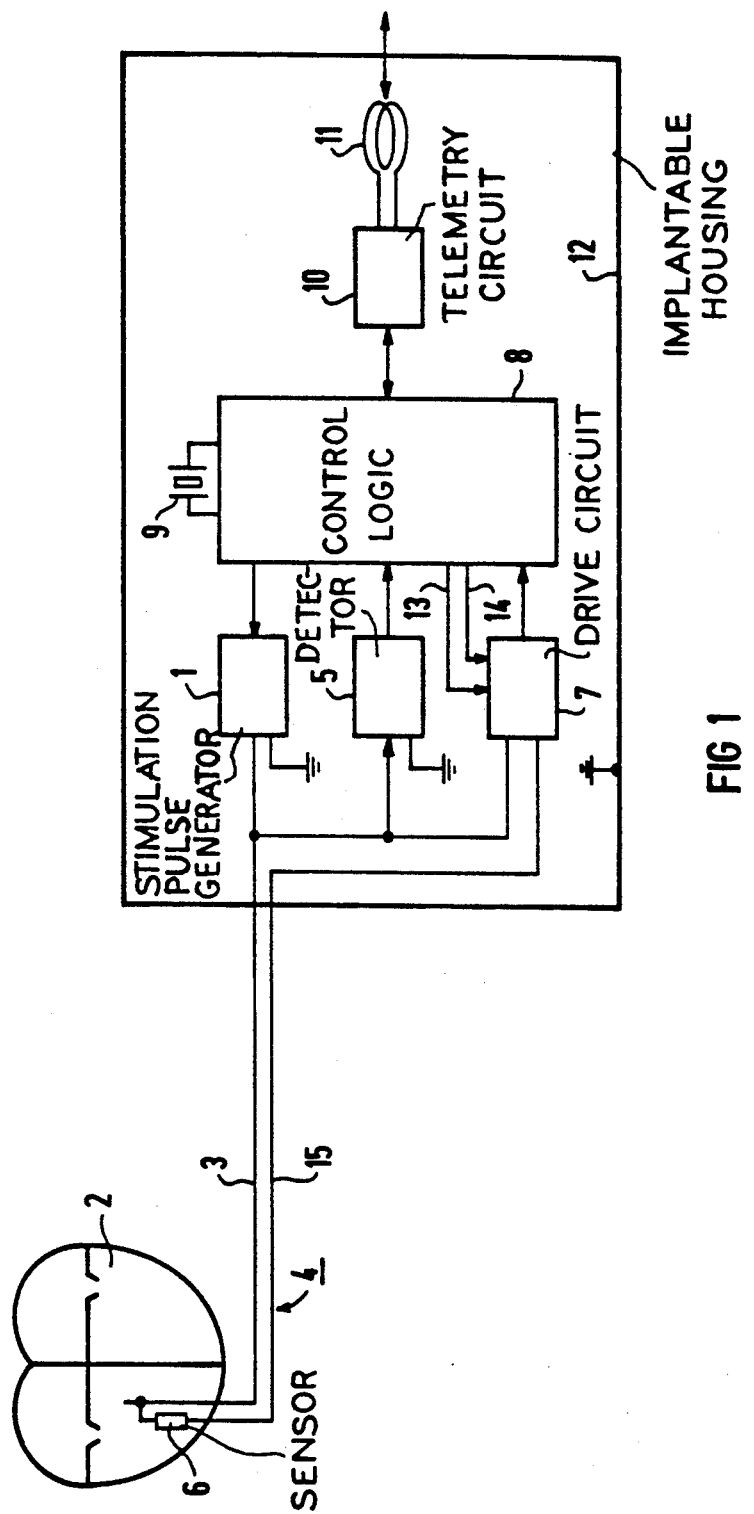
FIG. 1 is a schematic block diagram of a heart pacemaker which contains a measuring instrument apparatus constructed in accordance with the principles of the present invention.

For exemplary purposes for explaining the principles of the invention, a measuring instrument constructed in accordance with the principles of the present invention is embodied in a cardiac pacemaker shown in FIG. 1. The pacemaker contains a stimulation pulse generator 1 for generating electrical stimulation pulses in a known manner. The pulses are supplied to the heart 2 (schematically indicated) to be stimulated via an intracardial electrode 4 via a conductor 3 (for bipolar pacing, an additional conductor may be contained in the electrode 4). The free end of the electrode 4 is implanted in the right ventricle of the heart 2, accessible through the vein system.

In a known manner, a detector 5 for the detection of natural heartbeats is provided, the input thereof being connected to the conductor 3 of the electrode 4.

An apparatus for the formation of a measured signal corresponding to the physical activity of the patient in whom the pacemaker is implanted is also provided, this measuring instrument including a sensor 6 arranged disposed at the end of the electrode 3 implanted in the heart 2, and also include a drive circuit 7 for the sensor 6.

The stimulation pulse generator 1, the detector 5 and the drive circuit 7 are connected to a control logic 8, to which a crystal oscillator 9 is also connected for generating the clock and timing signals required for operation of the pacemaker. A telemetry circuit 10 is also connected to the control logic 8 in a known manner, the telemetry circuit 10 being connected to a transmission/reception coil 11. All of these electronic components are contained in an implantable, hermetically sealed housing 12. By means of the telemetry circuit 10 and the coil 11, communication between the implanted components and an external device (not shown in FIG. 1), known as a programmer, can be undertaken for the exchange and modification of data stored in the control logic 8. For this purpose, a transmission/reception coil of the programmer will be brought into proximity with the coil 11 in the housing 12 so that the two coils are inductively coupled.

Because the stimulation pulse generator and the detector 5 are in communication with the heart 2 to be stimulated only via one conductor 3 of the electrode 4, the reference potential is applied to the body of the patient via the electrically conductive housing 12 of the pacemaker. This is shown in FIG. 1 by the housing 12 as well as a terminal of the stimulation pulse generator 1 and a terminal of the detector means 5 being grounded.

The control logic 8 controls the cooperative operation of the stimulation pulse generator 1, the detector 5 and the sensor 6 together with drive circuit 7, so that the stimulation pulse generator 1 supplies a stimulation pulse as an output when the detector 5 has not detected a natural heart beat before the expiration of a defined time interval. The duration of the defined time interval is dependent on the physical activity of the patient identified with the sensor 6 and the drive circuit 7. The control logic 8 thereby modifies the duration of the defined time interval so that this interval becomes shorter with increasing physical activity. The stimulation rate with which successive stimulation pulses are supplied as needed thus increases with increasing physical activity. It is thus assured that the heart beat rate of the stimulated heart 2, similar to a healthy heart, will increase in the presence of increasing physical stress and will decrease in the presence of decreasing physical stress. Further details regarding the operation of cardiac pacemakers whose stimulation rate can be controlled in a stress or activity-dependent manner can be found in the publication "Sensor Controlled Pulse Generator SENSOLOG 703"-Physician's Manual, Siemens-Elema AB, Pacemaker Division, Solna, Sweden.

The sensor 6 is connected to the drive circuit 7 via the conductor 3 and via a further conductor 15, also contained in the electrode 4. The sensor 6 generates a measured signal which is supplied to the control logic 8 by the drive circuit 7. The measured signal may contain a signal component corresponding to the blood oxygen content and/or a signal component corresponding to the blood temperature. Via a control line 13 leading from the control logic 8 to the drive circuit 7, the control logic 8 can influence the operation of the drive circuit 7 so that the drive circuit 7 optionally operates in combination with the sensor 6 so that any one of a measured signal dependent on blood oxygen content and blood temperature, a measured signal dependent only on the blood oxygen content, or a measured signal dependent only on the blood temperature, is available. Three fundamentally different characteristics can thus be set for forming the measured signal which reflects the physical activity of the patient in whom the pacemaker is implanted. Switching among the various characteristics can be undertaken telemetrically by means of the programmer via the coil 11 and the telemetry circuit 10. The control logic 8 includes control circuitry for setting a suitable characteristic of the measured signal dependent on the intensity of the existing physical activity. In this operating mode, which can be also set telemetrically, the control logic 8 monitors the heartbeat or stimulation rate and sets the characteristics which influence the measured signal so that the signal is dependent only on the blood oxygen content for low physical activity levels and is only temperature-dependent for extremely high physical activity levels. In a transition region of moderate physical activity, the control logic 8 sets a characteristic so that the measured signal is dependent on both blood oxygen content and blood temperature.

Following the detection of a natural heartbeat or the output of a stimulation pulse, the control logic 8 activates the drive circuit 7 via a control line 14 for the duration which is required to form the measured signal. A power-saving operation of the measuring instrument is achieved in this manner, because the measuring instrument is only intermittently operated. During that time span wherein the measuring instrument is activated, moreover, the stimulation pulse generator 1 and the detector 5 are disconnected from the conductor 3 in a known manner (not shown). The measuring instrument is preferably active during the absolute refractory time (as defined, for example, in the above-identified Physician's Manual), during which it is already intended that neither stimulations nor detections will take place.

Figure 2:
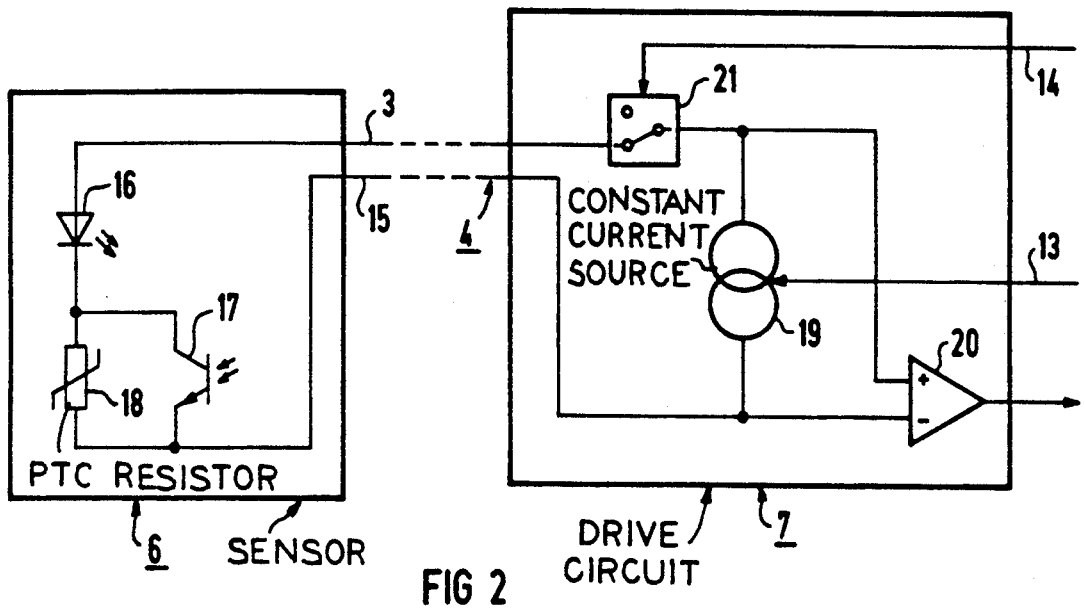
FIG. 2 is a circuit diagram of a sensor and a drive circuit for use in a pacemaker as shown in FIG. 1, in an embodiment making use of a constant test current.

A first embodiment of a measuring instrument constructed in accordance with the principles of the present invention is shown in detail in FIG. 2, the sensor 6 being shown connected to the drive circuit 7 via the electrode 4. For clarity, neither the connections of the conductor 3 to the stimulation pulse generator 1 and the detector 5, nor the end of the conductor 3 which is in contact with the heart muscle tissue to be stimulated (given an implanted electrode 4) are shown. The sensor 6 contains means for forming a signal component corresponding to the blood oxygen content of the subject in whom the heart pacemaker is implanted, the means forming a signal corresponding to the blood oxygen content, in the embodiment of FIG. 2, including a red light emitting diode 16 as a light transmitter and an npn phototransistor 17 as a light receiver. The light-emitting diode 16 and the phototransistor 17 are integrated into the electrode 4 so that the light-emitting diode 16 emits light into the venous blood of the subject, and the phototransistor 17 receives the portion of the emitted light reflected by the venous blood. The intensity of the reflected light represents a measure for the blood oxygen content of the venous blood, as is known in the art and is described, for example, in German Patent 3 152 963.

The sensor 6 also contains a PTC resistor 18 which serves the purpose of forming a signal component corresponding to the blood temperature of the venous blood. The PTC resistor 18 is integrated in the electrode 4 so that good thermal conduction is established between the venous blood and the PTC resistor.

The aforementioned components of the sensor 6 are combined to a two-terminal network with the light-emitting diode 16 and the PTC resistor 18 connected in series, and the photodiode 17 connected in parallel with the PTC resistor 18.

The electrode 4 has a further conductor 15, and the two-terminal network is connected via the conductors 3 and 15 to the drive circuit 7. In the embodiment of FIG. 2, the drive circuit 7 contains a constant current source 19 connected to the conductors 13 and 15. A test current supplied by the constant current source 19, as schematically shown in FIG. 2, is adjustable via the control line 13. The voltage drop across the sensor 6 as a consequence of the test current supplied by the constant current source 19 is amplified with an operational amplifier 20, schematically shown in FIG. 2, having inputs connected to the conductors 13 and 15. The output of the amplifier 20 is supplied as the measured signal to the control logic 8 (not shown in FIG. 2). To limit current flow through the sensor 6 to those time intervals wherein the measuring instrument is activated, the drive circuit 7 contains an electronic switch 21, which can disconnect the conductor 3 from the constant current source 19. The electronic switch 21 is activated by the control logic 8 as described above via the control line 14.

When the test current, referenced below as i, supplied by the constant current source 19 is limited to values of at most 0.2 mA, the light-emitting diode 16 no longer emits sufficient light for a signal component corresponding to the blood oxygen content to be formed. Consequently, when the sensor 6 is operated with a test current of at most 0.2 mA, only the signal component dependent on the blood temperature is formed, resulting in the measuring instrument having a characteristic which is exclusively dependent on the blood temperature.

Because the light-emitting diode 16 has a forward conducting voltage $V_{LED}$ which is substantially independent of the test current flowing through the light-emitting diode 16, but does have a temperature coefficient $TC_{LED}$ of $-2.5 \times 10^{-3}$ V/°C., which is opposite in operational sign with respect to the temperature coefficient $TC_{PTC}$ of the PTC resistor 18, for example, $0.8 \times 10^{-2}$°C.$^{-1}$, a value for the test current i. can be found at which the temperature responses of the light-emitting diode 16 and of the PTC resistor 18 exactly cancel each other. This is the case when $$\Delta V_{PTC} + \Delta V_{LED} = 0 \qquad (1)$$

applies, with $\Delta V_{PTC}$ and $\Delta V_{LED}$ respectively being in the changes in the voltage drop-off across the PTC resistor 18 and the light-emitting diode 16 caused by a defined temperature change $\Delta T$. The following equations are also applicable:

$$\Delta V_{PTC} = i \cdot (\Delta T \cdot TC_{PTC} \cdot R_{PTC}) \qquad (2)$$

and $$\Delta V_{LED} = \Delta T \cdot TC_{LED} \qquad (3)$$

wherein $R_{PTC}$ is the nominal resistance of the PTC resistor 18, for example $10^3$ ohms.

By introducing equations (2) and (3) into equation (1), one obtains $$i \cdot (\Delta T \cdot TC_{PTC} \cdot R_{PTC}) + (\Delta T \cdot TC_{LED}) = 0.$$

After factoring $\Delta T$, and resolution according to i and introduction of the above numerical values, the following value for i is obtained:

$$i = (2.5 \times 10^3)/(0.8 \times 10^2 \times 10^3) = 0.3125 \text{ mA}.$$

It is thus clear that the measuring instrument has a substantially temperature-independent characteristic, i.e. a characteristic which is exclusively dependent on the blood oxygen content, when the control logic 8 sets the constant current source 19 to a test current i of approximately 0.3 mA.

It is also clear that the measuring instrument will deliver a measured signal which is dependent both on blood oxygen content and on blood temperature with a test current i set by the control logic 8 which is greater than 0.2 mA which deviates from 0.3 mA.

The measuring instrument in the embodiment of FIG. 3 differs from that described in connection with FIG. 2 in that the drive circuit 7 in the embodiment of FIG. 3 contains a constant voltage source 22, with which a constant test voltage, which can be set via the control line 13, is supplied to the sensor 6 via the conductors 13 and 15 of the electrode 4. A shunt resistor 23 is connected in the line leading to the conductor 15. The voltage drop across the shunt resistor 23, which corresponds to the current flowing through the sensor 6, is amplified by a schematically indicated operational amplifier 24, and is supplied to the control logic 8. Further, the drive circuit 7 in the embodiment of FIG. 3 contains an electronic switch 25 connected between the constant voltage source 22 and the conductor 3, which is driven by the control logic 8 via the control line 14 so that a conductive connection of the constant voltage source 22 to the conductor 3 is present only when the measured signal is to be formed. In this manner, current flows through the sensor 6 only when it is desired that a measured signal be formed.

Figure 3:
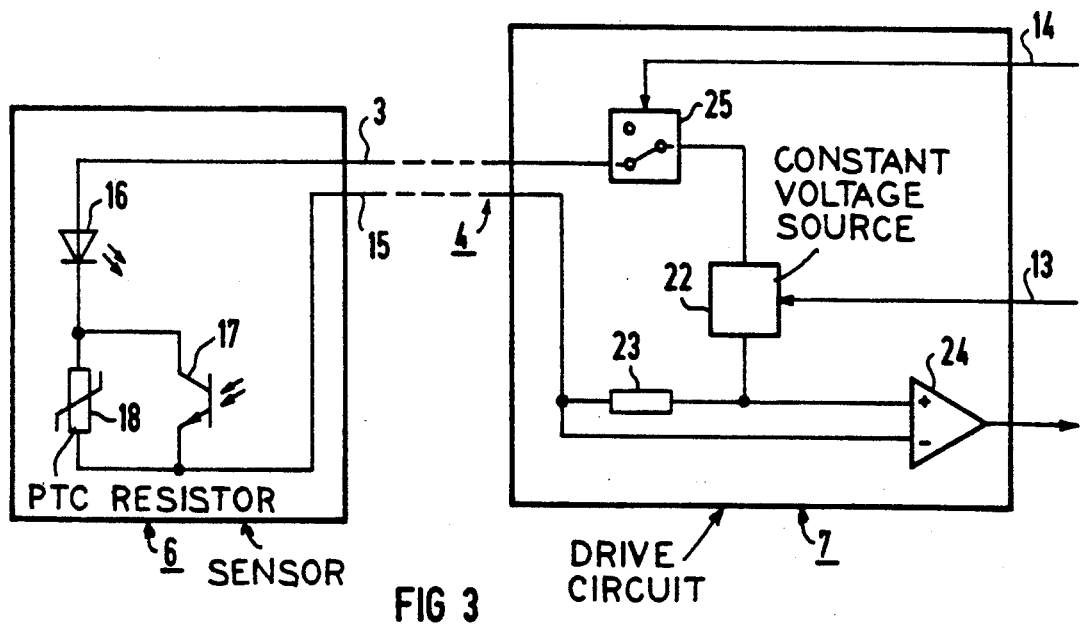
FIG. 3 is a circuit diagram of a sensor and a drive circuit for use in the pacemaker of FIG. 1 in an embodiment making use of a constant test voltage.

As a consequence of the electronic components of the sensor 6 being interconnected to form a two-terminal network in both the embodiments of FIG. 2 and FIG. 3, only two conductors 3 and 15 between the sensor 6 and the drive circuit 7, contained in the housing 12, are required. One of these conductors also serves the purpose of conducting stimulation pulses to the heart 2 or for supplying signals to the detector 5 corresponding to the electrical activity of the heart 2.

Although the measuring instrument of the invention has been described above in the context of a cardiac pacemaker, it can be used in any medical context wherein signals corresponding to blood oxygen content and/or blood temperature are desired. If the measuring instrument is used in the context of a medical apparatus which does not have an electrode associated therewith, the light emitting diode 16, the phototransistor 17 and the PTC resistor 18 can be integrated into the end of a catheter which contains a two-pole line for connecting those components to the drive circuit 7.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for in vivo intracardial acquisition of a measured signal corresponding to the level of physical activity of a subject, said apparatus comprising:
   first means for converting an electrical test signal into a first electrical signal component dependent on the blood oxygen content of said subject, the degree of dependence being dependent on the value of said test signal;
   second means for converting said electrical test signal into a second electrical signal component dependent on the blood temperature of said subject, the degree of dependence being dependent on the value of said test signal;
   said first means and said second means for converting being electrically combined in a circuit having only two terminals;
   control circuitry coupled to said two terminals including drive circuit means for supplying said test signal to said first and second means for converting, and further including measuring means for generating a measured signal which includes said first and second signal components depending on blood oxygen content and blood temperature;
   said test signal having a range of values including a first value below which said measured signal is significantly more dependent on blood temperature than on blood oxygen content and including a second value at which said measured signal is significantly more dependent on blood oxygen content than on blood temperature; and
   means for adjusting said test signal to a value within said range including said first value and said second value.

2. An apparatus as claimed in claim 1 wherein said drive circuit means is a means for supplying an adjustable constant voltage to said two terminals and wherein said measuring means is a means for deriving said measured signal from current drawn by said first and second means.

3. An apparatus as claimed in claim 1 wherein said drive circuit means is a means for supplying an adjustable constant current to said first and second means and wherein said measuring means is a means for deriving said measured signal from a voltage drop between said two terminals.

4. An apparatus as claimed in claim 1 wherein said first means includes light transmitter means operated by said test signal for emitting light into the blood of said subject to an extent dependent on the value of said test signal and light receiver means for receiving light from said light transmitter means reflected from said blood, and wherein, when said test signal has a value at or less than said first value, substantially no light is emitted by said light transmitter means so that said signal component dependent of the blood oxygen content is substantially zero, and said measured signal is independent on blood oxygen content, and light is emitted by said light transmitter means when said test signal has a value greater than said first value so that said measured signal is also dependent on the blood oxygen content.

5. An apparatus as claimed in claim 1 wherein said first means includes a light emitting diode operated by said test signal, wherein said second means is a PTC resistor connected in series with said light emitting diode between said two terminals, wherein said first means further includes a phototransistor connected in parallel with said PTC resistor, and wherein said drive circuit means is a means for supplying an adjustable constant test current to said two terminals.

6. An apparatus as claimed in claim 1 wherein each of said light transmitter means and said light receiver means comprises a photoconductor element.

7. An apparatus as claimed in claim 1 wherein said temperature sensor means is a means having a resistance which is temperature-dependent.

8. An apparatus as claimed in claim 1 wherein said drive circuit means is a means for supplying a pulsed test signal of constant magnitude to said two terminals.

9. An apparatus as claimed in claim 1 further comprising: means for controlling the stimulation rate of a heart pacemaker dependent on said measured signal.

10. An apparatus as claimed in claim 9 further comprising means for controlling said test signal of said drive circuit means dependent on the existing stimulation rate of said heart pacemaker.

11. An apparatus for in vivo intracardial acquisition of a measured signal corresponding to the level of physical activity of a subject, said apparatus comprising:
first means for converting an electrical test signal into a first electrical signal component dependent on the blood oxygen content of said subject, said first means having a temperature coefficient associated therewith;
second means for converting said electrical test signal into a second electrical signal component dependent on the blood temperature of said subject, said second means having a temperature coefficient associated therewith which is opposite in operational sign with respect to the temperature coefficient of said first means;
said first means and said second means being electrically combined in a circuit having only two terminals;
control circuitry coupled to said two terminals including drive circuit means for supplying said test signal to said first and second means, and further including measuring means for generating a measured signal which includes said signal first and second components depending on blood oxygen content and blood temperature;
said test signal having a range of values including a single value at which the temperature influences of said first and second means cancel each other so that said measured signal is dependent on blood oxygen only, with said measured signal also being dependent on blood temperature at all other values in said range; and
means for adjusting said test signal within said range including said single value.

12. An apparatus as claimed in claim 11 wherein said drive circuit means is a means for supplying an adjustable constant voltage to said two terminals and wherein said measuring means is a means for deriving said measured signal from current drawn by said first and second means.

13. An apparatus as claimed in claim 11 wherein said drive circuit means is a means for supplying an adjustable constant current to said first and second means and wherein said measuring means is a means for deriving said measured signal from a voltage drop between said two terminals.

14. An apparatus as claimed in claim 11 wherein said first means includes light transmitter means operated by said test signal for emitting light into the blood of said subject to an extent dependent on the value of said test signal and light receiver means for receiving light from said light transmitter means reflected from said blood, and wherein when said test signal has a value at or less than said first value substantially no light is emitted by said light transmitter means so that said signal component dependent on the blood oxygen content is substantially zero, and said measured signal is independent on blood oxygen content, and light is emitted by said light transmitter means when said test signal has a value greater than said first value so that said measured signal is also dependent on the blood oxygen content.

15. An apparatus as claimed in claim 11 wherein said first means includes a light emitting diode operated by said test signal, wherein said second means is a PTC resistor connected in series with said light emitting diode between said two terminals, wherein said first means further includes a phototransistor connected in parallel with said PTC resistor, and wherein said drive circuit means is a means for supplying an adjustable constant test current to said two terminals.

16. An apparatus as claimed in claim 11 wherein each of said light transmitter means and said light receiver means comprises a photoconductor element.

17. An apparatus as claimed in claim 11 wherein said temperature sensor means is a means having a resistance which is temperature-dependent.

18. An apparatus as claimed in claim 11 wherein said drive circuit means is a means for supplying a pulsed test signal of constant magnitude to said two terminals.

19. An apparatus as claimed in claim 11 further comprising: pacing means for electrically stimulating a heart at a stimulation rate; and means for controlling the stimulation rate of said pacing means dependent on said measured signal.

20. An apparatus as claimed in claim 11 further comprising means for controlling said test signal of said drive circuit means dependent on the existing stimulation rate of said pacing means.

* * * * *